US008682448B2

(12) United States Patent
Weinstock

(10) Patent No.: US 8,682,448 B2
(45) Date of Patent: Mar. 25, 2014

(54) EMF PROBE CONFIGURATIONS FOR ELECTRO-MODULATION OF IONIC CHANNELS OF CELLS AND METHODS OF USE THEREOF

(75) Inventor: Ronald J. Weinstock, Fort Lauderdale, FL (US)

(73) Assignee: EMC2 Holdings LLC, Charlestown, Nevis (BW)

( * ) Notice: Subject to any disclaimer, the term of this patent is extended or adjusted under 35 U.S.C. 154(b) by 193 days.

(21) Appl. No.: 13/065,015

(22) Filed: Mar. 11, 2011

(65) Prior Publication Data

US 2011/0224480 A1   Sep. 15, 2011

Related U.S. Application Data

(60) Provisional application No. 61/340,058, filed on Mar. 11, 2010.

(51) Int. Cl.
*A61N 1/18* (2006.01)

(52) U.S. Cl.
USPC ............................................ 607/65

(58) Field of Classification Search
USPC .................................. 607/65, 117
See application file for complete search history.

(56) References Cited

U.S. PATENT DOCUMENTS

| 5,000,178 | A | 3/1991 | Griffith |
| 5,374,283 | A | 12/1994 | Flick |
| 5,573,552 | A | 11/1996 | Hansjurgens |
| 6,014,585 | A | 1/2000 | Stoddard |
| 6,085,115 | A | 7/2000 | Weaver et al. |
| 6,546,290 | B1 | 4/2003 | Shloznikov |
| 7,117,034 | B2 | 10/2006 | Kronberg |
| 7,353,058 | B2 | 4/2008 | Weng et al. |
| 2001/0039375 | A1 | 11/2001 | Lee et al. |
| 2004/0176805 | A1 | 9/2004 | Whelan |
| 2004/0257747 | A1 | 12/2004 | Stevenson et al. |
| 2005/0177201 | A1 | 8/2005 | Freeman |
| 2005/0240239 | A1 | 10/2005 | Boveja et al. |
| 2007/0106342 | A1 | 5/2007 | Schumann |
| 2007/0249959 | A1 | 10/2007 | Kiefer et al. |
| 2008/0085265 | A1 | 4/2008 | Schneider et al. |
| 2009/0043188 | A1 | 2/2009 | Rauscher |
| 2009/0292333 | A1 | 11/2009 | Errico |

FOREIGN PATENT DOCUMENTS

WO   WO 2007/138595   12/2007

*Primary Examiner* — Joseph Dietrich
(74) *Attorney, Agent, or Firm* — Melvin K. Silverman

(57) ABSTRACT

A system for pattern recognition of cell and tissue malfunction and for treatment of such malfunction is presented. When a malfunction is recognized by a search signal or field, it is expressed as a waveform and an audio transform thereof. A malfunction pattern generally appears as a weak or static signal and, in audio terms, as a screeching sound. A complex EM wave and energy pattern is then re-iteratively applied to the location of the malfunction pattern until the pattern is normalized. A normalized pattern appears as a stronger more uniform waveform and a lower pitched audio of uniform amplitude. The mechanism of action of the process entails the correction of voltaic gradient errors across ionic channels of cells of tissues that are afflicted. Different conditions implicate different channels and cells. The system corrects undesirable voltage gradients across the cell membranes to restore normal flow of one or more categories of anions in or out of channels of cell membranes.

16 Claims, 16 Drawing Sheets

PEAK CALCIUM CURRENT

INTERNAL FREE $Ca^{2+}$

EMF PROBE CONFIGURATIONS FOR ELECTRO-MODULATION OF IONIC CHANNELS OF CELLS AND METHODS OF USE THEREOF

CROSS REFERENCE TO RELATED APPLICATION

This application claims the benefit under 35 USC 119(e) of the provisional patent application Ser. No. 61/340,058 filed Mar. 11, 2010, entitled EMF Probe Configurations for Electro-Modulation of Ionic Channels of Cells and Methods of Use Thereof, which is hereby incorporated by reference in its entirety.

BACKGROUND OF THE INVENTION

A. Area of Invention

The present invention relates to electromedicine, and more particularly, to the application of electrical and magnetic fields to tissue and the subsequent modulation of ionic flow, voltage gradient and other and electromagnetic properties of the tissue to recognize and treat abnormalities associated and with specific disease or pain condition.

B. Prior Art

A movement of electrons, about an atom's nucleus, generates specific ionic interactions and energy emissions, thereby resulting in an ion-based electromagnetic signature pattern of the atom. The electromagnetic signature patterns of multiple atoms are compounded into molecular electromagnetic signature patterns when the multiple atoms combine to form molecules. Similarly, the electromagnetic signature patterns of multiple molecules are compounded into cellular electromagnetic signature patterns when the multiple molecules combine to form cells. Consequently, a tissue, which is composed of multiple cells, has a characteristic electromagnetic signature or image pattern that is a cumulative result of individual electromagnetic signature patterns of the multiple atoms.

In case where the tissue is harmed, injured, diseased, or exhibiting pain, its electromagnetic signature pattern exhibits an abnormality, generally reflective of abnormal ionic cell gradient which leads to abnormal functioning of the tissue, structural damage or even death of the cells. A major cause of is an abnormal movement of electrons, which abnormally alters the shape of the atoms, which further alters the membrane structure and ionic balance of the molecule, which in-turn alters the normal functioning and chemistry of the cell, thereby resulting in cell damage, and/or cell death.

Diverse research has shown that the cellular functions of the tissues may be affected by magnetic stimuli. Weak magnetic fields exert a variety of biological effects, including causing alterations in cellular ion flux, and consequently affecting the electromagnetic signature pattern of the cells and subsequently, affecting the electromagnetic signature pattern of the tissues formed from those cells.

Conventionally, it is also known that electrical activity in some form is involved in many aspects of human physiology. For example, electrical activity has been measured during the regeneration of bone. In addition, it is well recognized that many cellular responses are dictated by electrical gradients generated in the cell (for example, nerve cells). Therefore, it is possible that exposure of the human body to an electromagnetic field could produce a beneficial physiological response in the body.

There exist several assumptions attending to the mechanism of the effect of low frequency magnetic field exposure on tissues. For example, low frequency magnetic field exposures have been proposed to exert their effect(s) through the induction of electric currents. Generally, research into magnet therapy is divided into two distinct areas, namely, pulsed bioelectric magnetic therapy and fixed magnetic therapy. It is estimated that probably 85 to 90 percent of the scientific literature is on pulsed bioelectric bio-magnetic therapy, and the remainder is on therapy with fixed solid magnets. There exist different theories regarding the essential mechanisms of magnetic therapy, most of which are focused on questions of polarity among other issues. However, fixed magnetic therapy has yet to be widely accepted by the scientific and medical community.

It is also well known that the concept of pulsed electromagnetic effects was first observed by the renowned scientist Michael Faraday in 1831. Faraday demonstrated that time varying magnetic fields have the potential to induce current in a conductive object. Faraday found that by passing strong electric current through a coil of wire, he was able to produce pulsed electrical effects. Such pulsed magnetic stimulus was able to induce the flow of current in a nearby electrically conductive body.

In the years following the discoveries of Faraday, pulsed electromagnetic stimulators have found application in certain areas of scientific investigation. For example, in 1965, the scientists Bickford and Freming demonstrated the use of electromagnetic stimulation to induce conduction within nerves of the face. Later, in 1982, Poison et al., as disclosed in U.S. Pat. No. 5,766,124 produced a device capable of stimulating peripheral nerves of the body. This device was able to stimulate peripheral nerves of the body sufficiently to cause muscle activity, recording the first evoked potentials from electromagnetic stimulation. Moreover, the application of extremely low frequency (less than 100 hertz) electromagnetic signals has beneficial therapeutic effects. See, for example, the paper "Therapeutic Aspects of Electromagnetic Fields for Soft-Tissue Healing" by B. F. Siskin and J. Walker, 1995 published in Electromagnetic Fields: Biological Interactions and Mechanisms, M. Blank editor, Advances in Chemistry Series 250, American Chemical Society, Washington D.C., pages 277-285, which at pages 280-81 discusses the effects on ligaments, tendons, and muscles of fields up to 1000 Gauss using EMF pulse trains of 1 to 500 Hz, over periods of up to ten weeks.

Further, as discussed previously, bone material may also be treated using electromagnetic and/or vibrational energies. Subsequently, pulsing electromagnetic fields have been widely used by orthopedic physicians to stimulate the healing of fracture non-unions. See, e.g., the 1995 article by Bassett entitled "Bioelectromagnetics in the Service of Medicine" published in Electromagnet Fields: Biological Interactions and Mechanisms, M. Blank editor, Advances in Chemistry Series 250, American Chemical Society, Washington D.C., pp. 261-275. One of the earliest practical applications of electromagnetic stimulating technology took the form of a bone growth stimulator a device that employed low frequency pulsed electromagnetic fields (PEMF) to stimulate bone repair.

In the past, pulsed electromagnetic stimulation devices have taken a number of different forms in attempts to treat various medical conditions. Generally, these different forms have resulted in two broad categories of coil arrangements for the generation of PEMFs: (1) planar or semi-planar designs with tightly wound coils, and (2) solenoid coils. Flat, wound coils create electromagnetic fields that degrade rapidly over a short distance as they pulse away from the inducing coil.

Prior art known to the inventor includes patent to Dissing et al, namely, U.S. Pat. No. 6,561,968, entitled "Method And An Apparatus For Stimulating/Modulating Biochemical Processes Using Pulsed Electromagnetic Fields," which discloses stimulating and/or modulating growth and differentiation in biological or plant tissue, seeds, plants, and microorganisms. Dissing discusses an apparatus including a pulse generator and a plurality of coils, in which pulsed currents cause fluctuating magnetic fields in a predetermined region holding the material to be stimulated. However, the apparatus is large and cumbersome and does not readily lend itself to private personal use.

U.S. Pat. No. 6,149,577 to Bouldin et al, entitled "Apparatus and Method For Creating a Substantially Contained, Finite Magnetic Field Useful For Relieving The Symptoms Pain And Discomfort Associated With Degenerative Diseases And Disorders. Bouldin does not teach any detecting mechanism for pain and discomfort associated with degenerative diseases and disorders.

Blackwell holds U.S. Pat. No. 6,186,941 entitled "Magnetic Coil for Pulsed Electromagnetic Field", which teaches use of portable PEMF coils for treatment of injuries in a patient.

U.S. Pat. No. 5,518,496 to McLeod relates to an apparatus and a method for regulating the growth of living tissue. The apparatus includes a deformable magnetic field generator and a magnetic field detector for producing a controlled, fluctuating, directionally oriented magnetic field parallel to a predetermined axis projecting through the target tissue.

U.S. Pat. No. 6,675,047 to Konoplev relates to a method of electromagnetic field therapy consists in that an organ or a whole organism and an apparatus for carrying out the method of the invention including a power supply source, a stabilizer, an antenna, a matching unit, a unit for shaping packets of radio pulses, made as a microprocessor controller with a permanent memory, a computer interface unit, a liquid-crystal display, and a keyboard.

U.S. Pat. No. 7,175,587 to Gordon relates to an apparatus and method for applying pulsed electromagnetic therapy to humans and animals. Gordon teaches a straight wire element that is employed to generate the magnetic field, and, a power and timer circuit that supplies current pulses that approximate square pulses in form, so that the straight wire element generates magnetic pulses having rapid rise and fall times.

U.S. Pat. No. 7,338,431 to Baugh relates to a system and method for stimulating the immune systems of biological entities in an environment are disclosed. Pulsed electrical currents are generated using an electric current generator. The pulsed electrical currents are fed through an arrangement of electrically conductive material such that magnetic energy is emitted from the arrangement into the environment.

Conventionally, techniques which have been used to treat injuries using PEMF include the use of Helmholtz and toroidal coils to deliver PEMF. Such methods and apparatuses generally suffer from various disadvantages. For example, Helmholtz coils suffer from field inhomogeneity and field dropoffs in certain zones (e.g., the field drops to zero near the center of the coil). Toroidal coils are inefficient and have relatively weak field strength. Additionally, known methods of PEMF treatment have problems associated with system complexity, large size and weight, long treatment times, weak PEMF strength and low efficiencies in promoting healing. Current devices and methods of PEMF treatment further fail to provide adequate mobility during treatment.

Recent developments in molecular cell biology have confirmed the principles reflected in the above material. For example, Jiang et al, Rockefeller University, 2002, states that Ion channels exhibit two essential biophysical properties: (a) selective ion conduction, and b) the ability to gate-open in response to an appropriate stimulus. Two general categories of ion channel gating are defined by the initiating stimulus: (a) ligand binding (neurotransmitter—or second-messenger-gated channels) and (b) membrane voltage (voltage-gated channels). The structural basis of ligand gating in a K+ channel is that it opens in response to intracellular $Ca2^+$. Jiang author reports he has they cloned, expressed, and analyzed electrical properties, and determined the crystal structure of a K+ channel from methanobacterium thermoautotrophicum in the (Ca2+) bound, opened state and that eight RCK domains (regulators of K+ conductance) form a gating ring at the intracellular membrane surface. The gating ring uses the free energy of Ca2+ binding to perform mechanical work to open the pore.

The molecular characterization of the neuronal calcium channel has been studied by Perez-Ryes. *Nature* 1998, 391: 896.

In addition to the above, a majority of the prior attempts to use electromagnetic therapy have used high levels of electromagnetism, usually 50 Gauss or more. While most of this therapy has used flat magnetic generators, a few have wrapped a magnetic blanket around a body member to attempt to regenerate or heal the body part. Some of the attempts have used pulsed waves, but such pulsed waves have been either on-off pulses or sinusoidal waves. Use of special spatial geometry EMF pulses is not known in the art.

Therefore, as may be seen, existing solutions are available to treat certain illness and disease, improvements in, additions to and complements of such treatments would enhance the quality of life and ameliorate or reduce symptoms associated with a variety of conditions. Henceforth, there exists a need for additional systems and methods capable of treating multiple disorders, abnormalities, and diseases, and/or complementing treatment of certain disorders, abnormalities, and diseases.

SUMMARY OF THE INVENTION

Thus, in accordance with various embodiments of the present invention, there is provided an EMF probe assembly and a method for treatment of recognizing and treating abnormalities of nerve and other cells in the human body including membrane flow of ions associated therewith. The EMF probe assembly comprises a probe, a plurality of cores, and a plurality of coils, where each coil of said plurality of coils is wound around each core of said plurality of cores. In a preferred embodiment, one probe is spherical, and is positioned centrally on a top surface of the EMF probe assembly. The probe produces an electromagnetic pulse train and an associated pulsed magnetic field. In accordance with an aspect of the present invention, said plurality of cores are ferrite cores and said plurality of coils are induction coils generate axial and hemispheric magnetic fields.

The method comprises placing said probe of said EMF probe assembly in contact with human tissue having a malfunctional or diseased state for first identifying and then imparting complex pulsed electromagnetic waves. The method may further comprise the step of determining a damaged or dysfunctional cellular area by inducing electrical and magnetic fields into the human tissue at different planes and polarities.

A malfunction pattern generally appears as a weak or static signal and, in audio terms, as a screeching sound. A complex EM wave and energy pattern is then re-iteratively applied to the location of the malfunction pattern until the pattern is normalized. A normalized pattern appears as a stronger more uniform waveform and a lower pitched audio of uniform amplitude. The mechanism of action of the process entails the correction of voltaic gradient errors across ionic channels of cells of tissues that are afflicted. Different conditions implicate different channels and cells. The system corrects undesirable voltage gradients across the cell membranes to restore normal flow of one or more categories of anions in or out of channels of cell membranes.

It is an object of the present invention to employ principles of pulsed electromagnetic waves for the analysis and treatment of abnormalities cells of soft and nerve cells in the human body.

It is yet another object to provide a system to analyze and digitize normal pulsed EM patterns of cells of specific tissues for purposes of treatment.

It is further object of the invention to normalize and correct complex electromagnetic wave abnormal patterns of tissues by applying a countervailing or neutralizing abnormal EM field spectra utilizing inductive sensors and means to apply EM patterns.

It is further object to provide a system of the above type in which pulsed EM wave pattern information is measured at a trigger point, at or near a tissue dysfunction or pain site, and a counter pattern is applied to said site to realign shifted and depressed patterns associated with the membranes of cells resultant of an abnormal or pain condition.

In accordance with another aspect of the present invention, there is provided a method, which employs the EMF probe assembly for treating abnormalities of cells of soft and nerve cells in the human body. The method may further comprise the step of treating a damaged or a particular dysfunctional cellular area or membranes thereof.

DETAILED DESCRIPTION OF THE INVENTION

Figure 1:
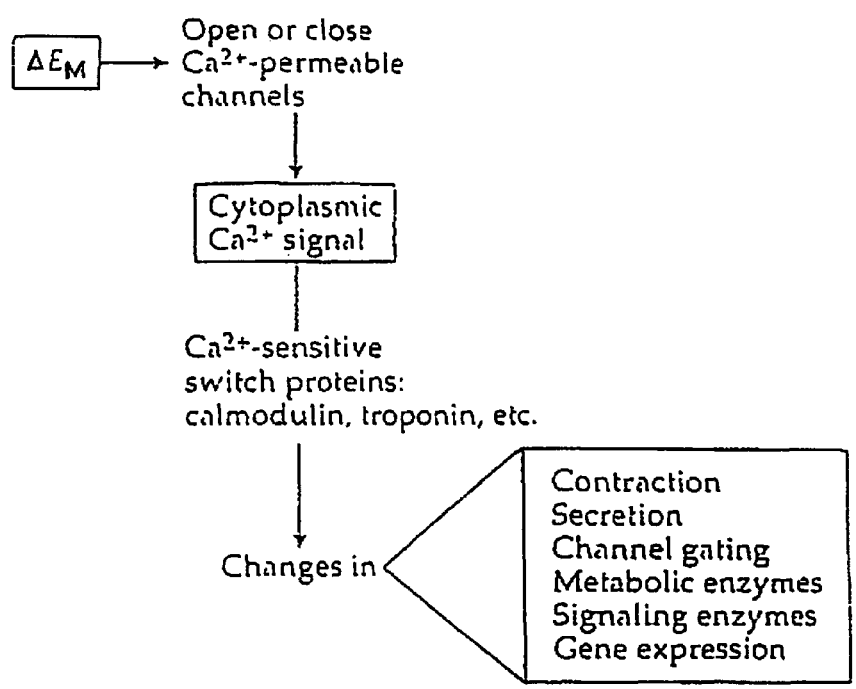
FIG. 1 is a flow diagram showing cytoplasmic calcium and other changes that occur when membrane potential changes are sensed by a cell.

FIG. 1 is a conceptual flow diagram illustrating a sequence of cellular events, which occur when a cell senses a voltage gradient carried or created by a calcium anion. The fact that cells of the human body are acutely responsive to electrical stimulation through neurotransmitters and otherwise, has long been established by research in the area. Calcium has been determined to be the final transmitter of electrical signals to the cytoplasm of human cells. More particularly, changes in cell membrane potential are sensed by numerous calcium-sensing proteins of cell membrane which determine whether to open or close responsive to a charge carrying elements, in this case, the calcium anion $Ca^{2+}$. Stated otherwise, calcium ions transduce electrical signals to the cells through what are termed voltage-gated calcium channels (see Hille, "Ion Channels of Excitable Membranes," 3 Ed., 2001, Chap. 4). It is now recognized that electrical signaling of voltage-gated channels (of which there are many categories) of human cell membranes is controlled by intracellular free calcium (and other) ionic concentrations, and that electrical signals are modulated by the flow of calcium anions into cytoplasm from the external medium or from intra cellular stores.

Figure 2:
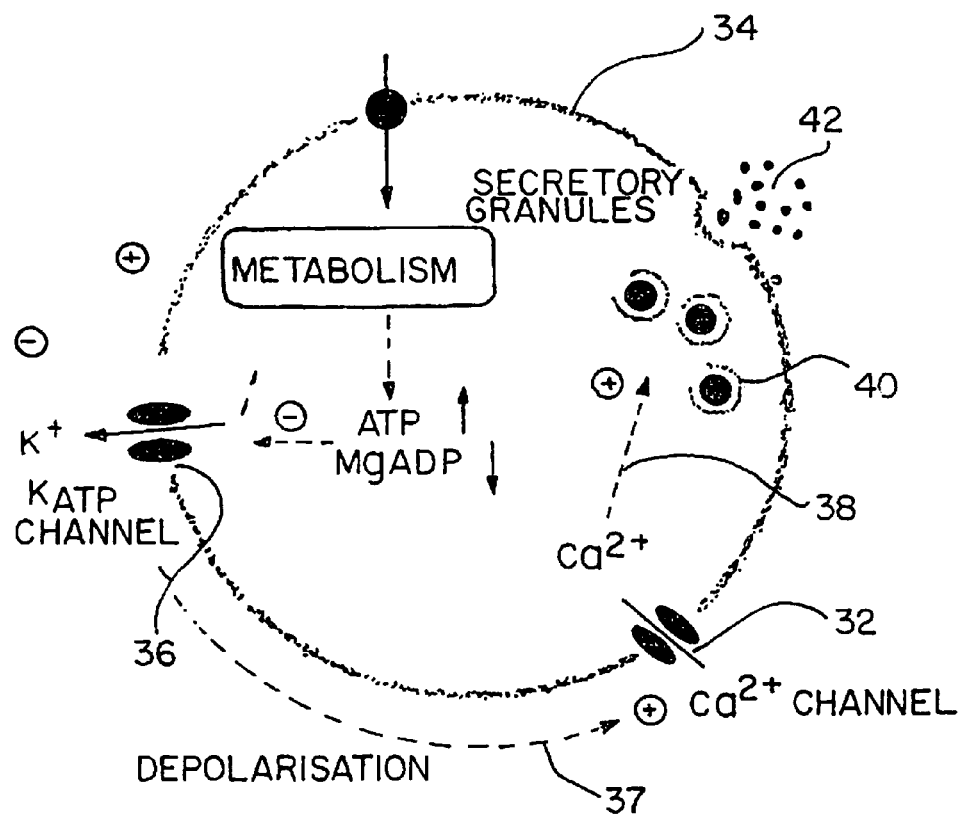
FIG. 2 is a diagrammatic view showing the role that the $Ca2^+$ and $K^+$ channels play in insulin secretion.

FIG. 2 illustrates a schematic view of a cellular level activity and a calcium ion channel of the cell. One well-studied calcium dependent process is the secretion of neuro-transmitters at nerve terminals which, of course, are associated with neuronic pain. See Hille, page 104 thereof. Within the presynaptic terminal of every chemical synapse, there are membrane-bounded vesicular-containing high concentrations of neurotransmitter molecules of various types. When such an action potential engages a neurotransmitter, the membranes having one or more of these vesicles in their surface membrane, release a group of neuro-transmitters into the cellular space. In the pancreas, for example, there exist so-called pancreatic acinar cells which contain zymogen granules which assist in cellular functions thereof.

Normally stimulated secretion from nerve terminals of most excitable cells require that extracellular calcium anions $Ca^{2+}$ pass through ionic channels of the cell. FIG. 2 illustrates the calcium ionic channel 32 of cell 34 as well as the egress of a potassium anion through a so-called KATP channel 36 when a calcium anion enters the cell. This process triggers a variety of functions which relate to pain response. FIG. 2 therefore illustrates the current module of signal secretion (Ashcroft, "Ion Channels and Disease," 2000, p. 155), as understood.

These changes act in concert to close calcium channels 36 in the beta-cell membrane because ATP inhibits, whereas MgADP (shown in FIG. 2) activates, calcium ion channel activity. In that calcium channel activity determines the cell resting potential, its closure causes a membrane depolarization 37 that activates voltage-gated calcium anion channels 32, increasing calcium. Insufficient charge upon intracellular calcium may, it is believed, be one cause of inhibition of various normal metabolic processes. In other words, if intracellular calcium, or its relevant neurotransmitters, lack sufficient charge, insufficient electrical energy 38 is provided to secretory granules 40 sufficient to facilitate many immulogic functions.

Another view of the above is that, by blockage of potassium ion channels 36, sufficient charge can be sustained within the cell to maintain normal function of secretory granules 40.

Aspects of this metabolism cause the potassium ATP channels 36 to close which results in membrane polarization 37, change of voltage potential at calcium ion channels 32, and an increase in cytoplasmic anionic calcium that triggers the function of secretory granules 40. It is therefore desirable to regulate calcium channel activity. This requires that the adequate molarity of $Ca^{2+}$ exist in most cells.

Figure 3:
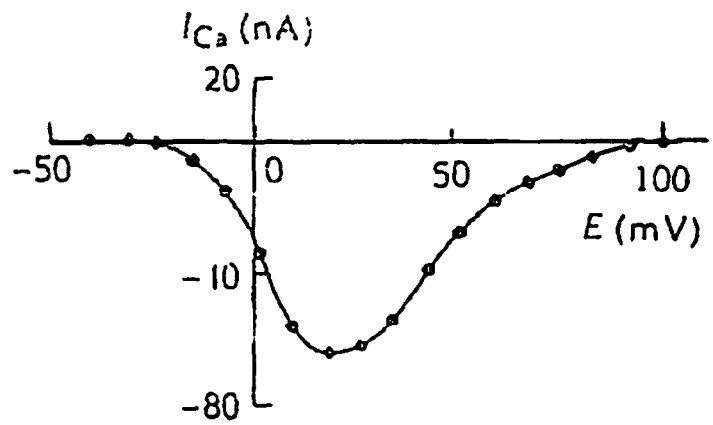
FIG. 3 is a graph showing the relationship between cell membrane potential, and calcium ion related current flow in a human cell.
Figure 4:
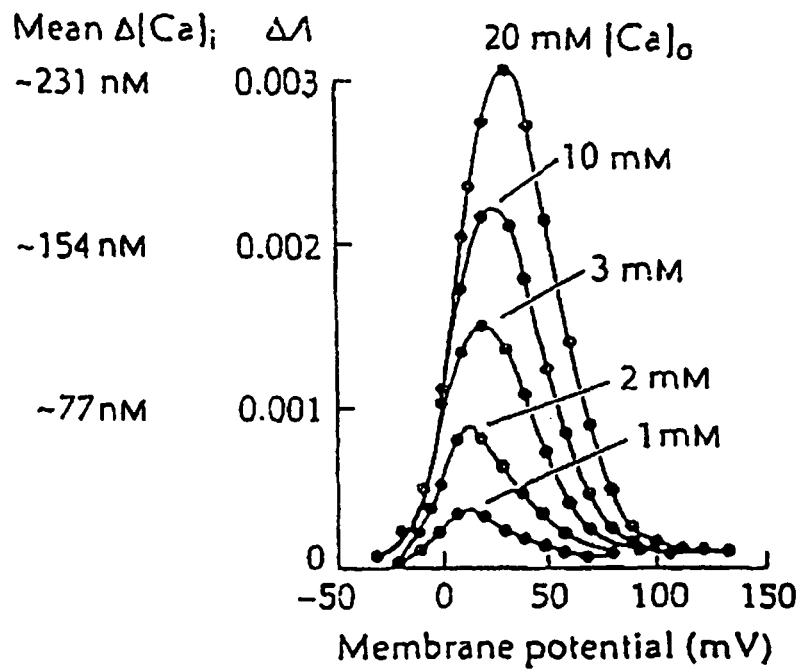
FIG. 4 is a graph showing the relationship between cell membrane potential and concentration of free calcium ions within a cell.
Figure 5:
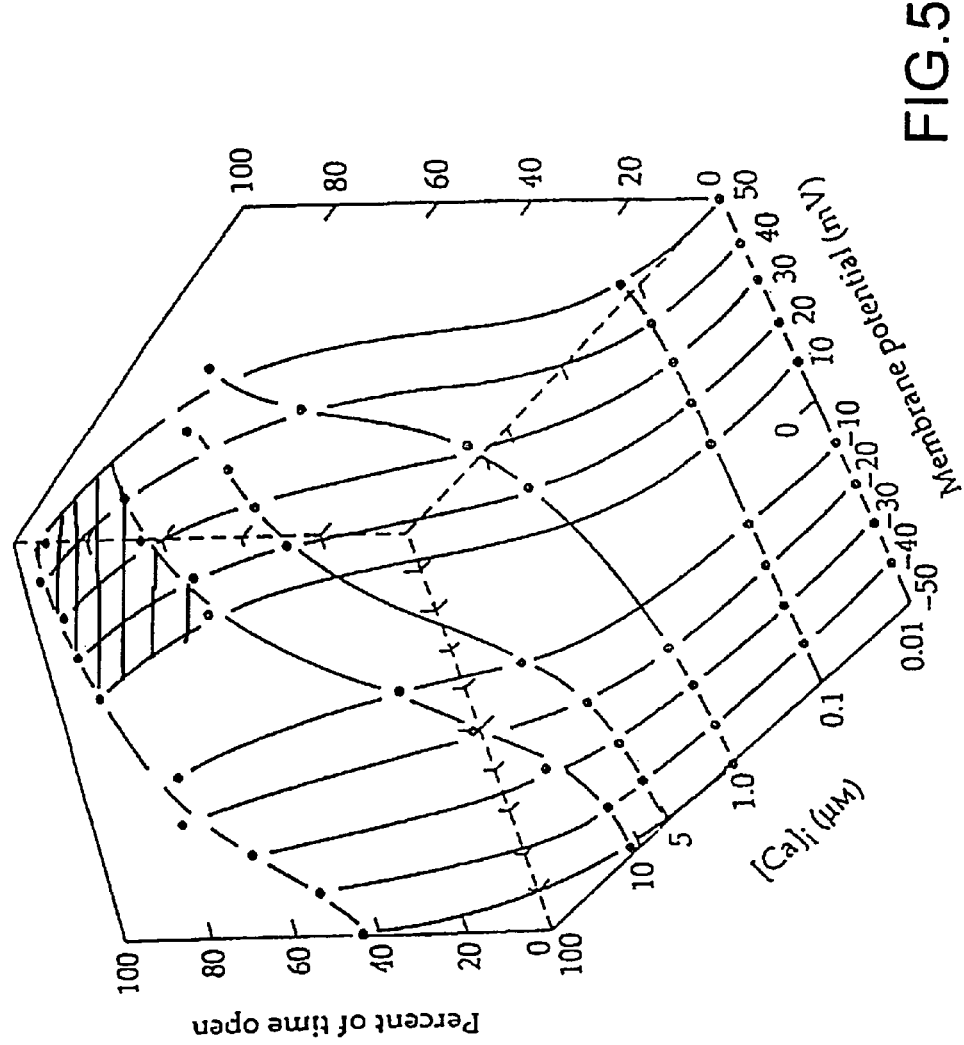
FIG. 5 is a three-dimensional graph showing the relationship between cell membrane potential, calcium ion related current flow into the, cell and percent of time that calcium gated channels of the cell are open.

FIGS. 3 and 4 illustrate a relation of the level of ionic calcium on membrane potential of the cell to ionic current flow within the cell, and molarity of calcium within the cell respectively. FIG. 5 graphically illustrates that the percent of time of calcium channel opening as a function of membrane potential and calcium molarity within the intracellular media. Stated otherwise, an increase in membrane potential will increase the time that voltage-gated ionic channels of the cell are open. In view of the above, it appears an appropriate increase in ionic calcium within certain cells will bring about an increase in immulogic function or resistance to neuronal damage if supported by sufficient membrane potential. The cross-hatched area at the top of FIG. 5 represents the confluence of the parameters most beneficial to health of the cell.

Potential choices of appropriate signals may be frequency critical as has been set forth by Sandblom and George, "Frequency Responsive Behavior of Ionic Channel Currents Modulated by AC Fields" (1993) who indicates that ionic channel currents are frequency-dependent and affect the rates of transports of ions through channels. Liboff et al have proposed an optimum fluctuating magnetic field frequency for regulating transport frequency regulating transport across ionic membrane. See U.S. Pat. No. 5,160,591 (1992).

Figure 6:
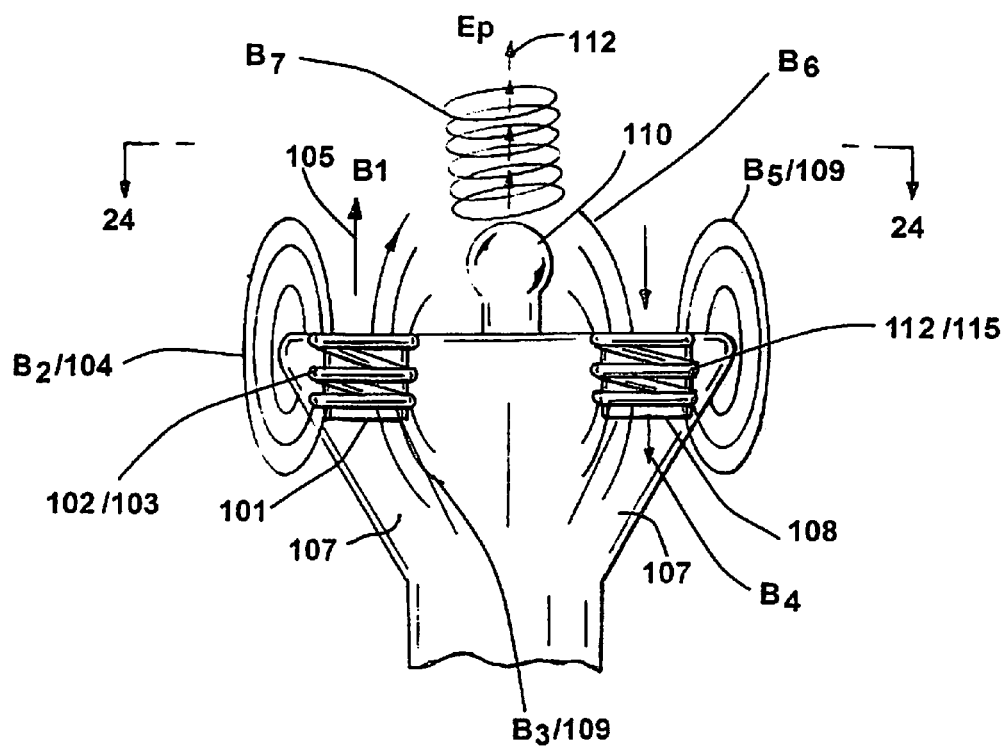
FIG. 6 is a side schematic view of an EMF probe assembly in accordance with the present invention.
Figure 7:
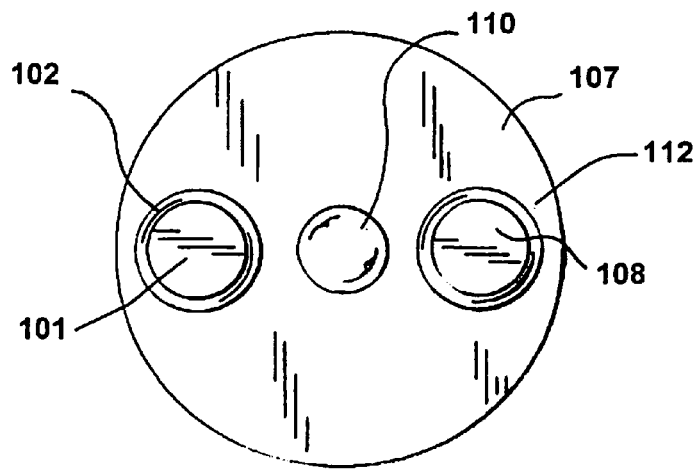
FIG. 7 is a top plan view of the assembly of FIG. 6.

FIGS. 6 and 7 illustrate a general appearance of probe 107 used in the practice of the inventive method of treatment of abnormalities of hard and soft tissue and nerve cells in the human body. The handle of probe 107 may be formed of a polymeric material such as ABS or any non-conductive equivalent thereof. Provided therein are preferably identical ferrite cores 101 and 108 around which are wound induction coils 102 and 112. Their magnetic fields may be axially variable if a pivot point for the middle of the axis of the cord is provided. The axial magnetic fields resultant of these structures as shown as arrows B1 and B4 in FIGS. 6 and 7, each of which however produces oval-like peripheral outer fields B2 and B5 as well as inner fields B3 and B6 which bend in the direction of a central spherical probe 110 (see FIGS. 6 and 8) of the structure. The direction of B4 is opposite to that of B1 because the respective directions of current flow therein are opposite. Said induction coils 102 and 112 will preferably produce an inductance and associated axial magnetic fields in a range of 0.5 to 1000 milliGauss. The lateral magnetic fields B2 and B5 associated with the coils and their ferrite cores would typically fall in a similar milliGauss range. Coils 102 and 112 are powered by a current at a frequency a range of 1 to 120 G Hertz, but the respective currents therein flow in opposite directions. See FIG. 8.

The axially disposed spherical probe 110 produces an electric pulse train Ep/112 and magnetic pulsed field B7, schematically shown as arrows and loops in FIG. 6 and as it would appear on an oscilloscope in FIG. 11, as set forth in the text below. These AC pulses generate an associated spiral magnetic field B7 shown in FIG. 6. The primary lines of pulsed magnetic field B7 are at right angles to the primary lines of magnetic flux B1 to B4 associated with the coils 102 and 112 above described. The fact that electrical pulse 112 is projected at a right angle, particularly to fields B1 and B4, will result in a so-called ExB vector force which contributes to the therapeutic effects described herein.

Spherical probe 110 therefore emits a complex pulsed EM wave into the treated tissue having, on one plane, the general pulse geometry shown in FIG. 11, as explained in the text below. For simplicity, aspects of the electrical signal 112 caused by the above-referenced cross-vector effect are not shown. However, it is to be appreciated that the waveform of FIG. 11 includes a magnetic component which projects transversely to the plane of the image shown in FIG. 11 prior to and during response from the tissue.

Following direct physical administration of probe 110 to soft tissue, or neuronal cells, complex respectively transverse electrical and magnetic fields will be induced into the treated tissue. This is the case whether the patient suffers from inflammation, blood loss, neurologic damage, fibrosis, devascularization, or a variety of other conditions. All will respond in a manner very generally depicted by wave forms 116/120 in FIG. 12. However, pattern segments 118 of low energy indicate a malfunction of the target tissue. Segments 120 indicate healthier cell function.

All waveforms are digitally converted to an audio transfer for use by the system technician or clinician. Generally, the degree of static, randomness, or weakness of signal 116/118/120 is an indication of a degree of cellular or tissue level dysfunction of some type. Often, visual static will be expressed as a screeching sound in the audio transform. More particularly, if the waveform shown in FIG. 12 does not exhibit a particular degree of dysfunction, that will generally indicate to the technician that probes 107 and associated fields have not contacted the damaged or dysfunctional area of the tissue. In such case, the technician slowly positions and re-positions the probe until both the time domain and amplitude level of the static segment 118 of the is maximized. In a typical treatment scenario, when the probes 107 are correctly located at the cellular area most damaged or dysfunctional, extreme static will be heard through the audio transform of signal 116/118/120. When the clinician hears such high amplitude and compressed time domain static, he will enhance the level of the applied signal 112 which becomes signals 401/408 in FIG. 13. This is the so-called treatment or healing signal of the present invention, the effectiveness of which is enhanced by the various magnetic fields B1 to B7, above discussed, as well as the cross-vector force associated with the interaction of electrical and magnetic fields projecting at right angle to each other. As such, the treatment of the invention is not simply unidirectional, or one defined by the directionality of EMF field Ep/112 (see FIG. 6) but, as well, by cross-directional magnetic and ExB forces which, it has been found, enhance healing and normalization of numerous dysfunctions including, without limitation, nerve bruises, soft tissue inflammation, including joint dysfunctions particular to arthritis. As such, the present therapy is invaluable in the treatment of much area which entails inflammation.

Macrophage invasion is reversed as is fibroblast proliferation, permitting revascularization and the growing of healthy new tissue. Regarding to the duration of treatment at a given treatment site, the instant protocol is to apply and increase the signal 112 or 403 to the highest level which the patient can tolerate until the response train 116 (see FIG. 12) moves above the axis stability indicating strength and stability. It has been found that after treatment with wave form 403 of FIG. 13, at the highest EMF level which the patient can tolerate, a return to normality of a particular tissue area treated, often occurs in a matter of just 10 to 15 seconds. The clinician then proceeds to locate other cells or tissue in the same area also associated with the malfunction. A few clusters of damaged cells will typically occupy a given treatment area. By searching for areas of static, as above described, the technician is able to treat damaged tissue or associated neurons to promote both healing of soft tissue and of nerve fibers. It has been found that a patient, treated three times a week for a period of about three weeks can experience substantially and permanent relief from a wide range of soft tissue and nerve-related dysfunctions.

It is to be appreciated that a goal of the product therapy is to normalize the components of the apparently random static signal (referenced above) by normalizing each of the constituent levels of dysfunction through the use of selective E and B fields and pulses. These produce induced currents, voltages and ExB forces in the tissue to be treated across the cell membranes of the treated tissue. The pulsed fields generated by the spherical probe 110 particularly the axial E field 112 component emitted by it has its greatest effect at the macro or tissue level.

The alternating B fields produced by the two lateral coils 102 and 112 will, under Faraday's Law, induce low level alternating E fields that will reach across the air gap (the height of the probe 110) to cells of the target tissue, or between probes. See FIG. 26. These low level E fields, in the millivolt range, affect the action potential of the ionic channels (some of which are paramagnetic), e.g., channels of the nociceptive neurons, thus causing these channels to expel sodium anions to the outside of the cell. Excessive intracellular sodium is a source of pain and inflammation. The low level E field will, it is believed, also help to open the calcium anion channels by increasing the millivolt level action potential of those channels, triggering an inflow of calcium anions, which effect also causes a K anion inflow to the cell. As such, a proper balance of sodium, calcium and potassium anions between the intra- and extra-cellular fluid is accomplished, reducing pain and inflammation.

Calcium anions are also a known second messenger of many cell functions. Thereby, normalizing the intra to extra cellular balance of calcium anions operates to normalize the second messenger functions thereof.

The effect of the ExB vector force is most likely that of a micro-vibration that operates as a micro-massage that helps to eject toxins from the target tissue.

The molecular manifestation of a disease would be seen in the smallest amplitude sinusoidal components of the static signal. At that level, disease appears as a distortion in the normal electron path or of the valance shell geometry of the molecule. Biologic molecules may be very large and complex. The lower energy effects of frequency, phase, amplitude and waveform of the various E and B induced fields function to correct these distortions of geometry of molecules of the target cells. As such, concurrent use of electrical and magnetic fields, inclusive of important interactions therebetween, maximize the healing function.

Figure 8:
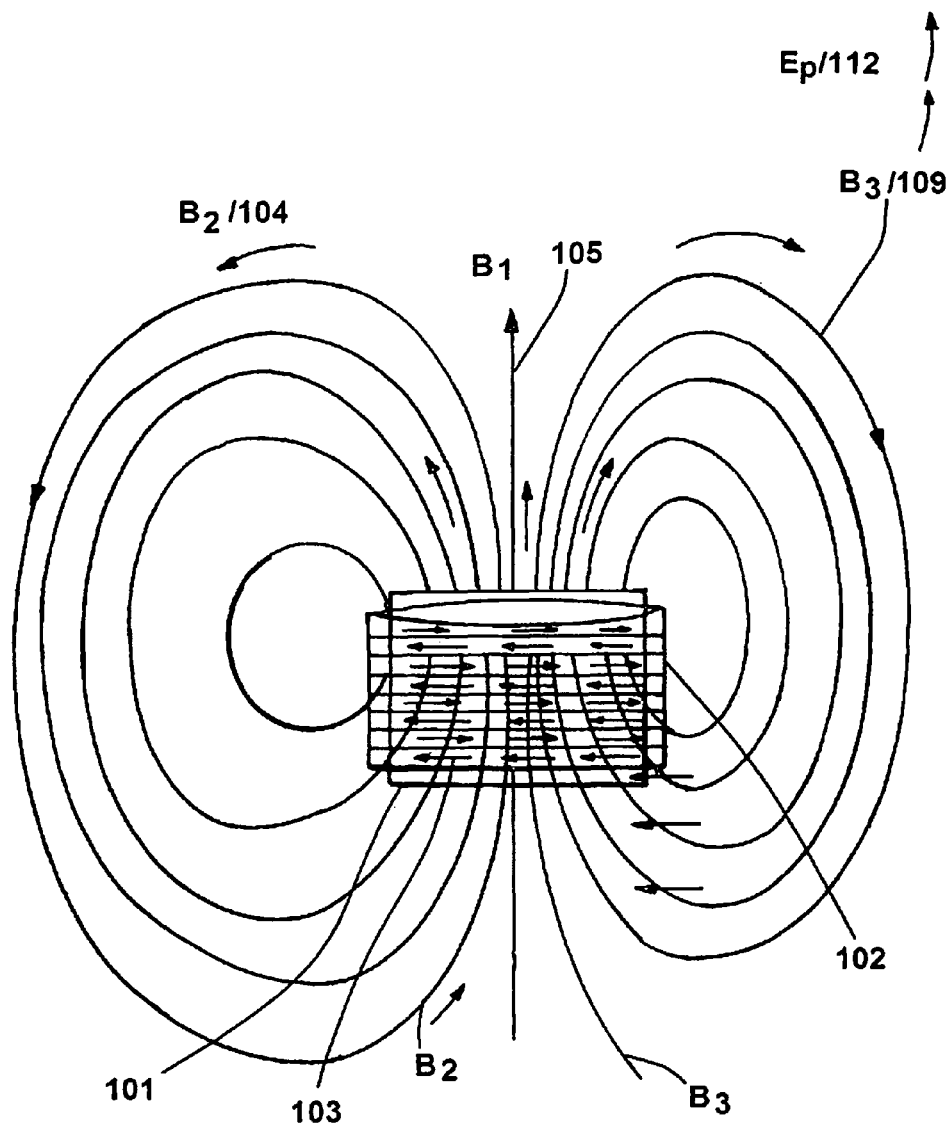
FIG. 8 is an enlarged schematic view of one of the inductive coil portions of the EMF probe assembly.

FIG. 8 illustrates a detailed view of the inductive coil 102 and its associated fields. Therein is shown the flow of current 103 within the coil 102, as well as radial field B1 and hemispherical fields B2 and B3.

Figure 9:
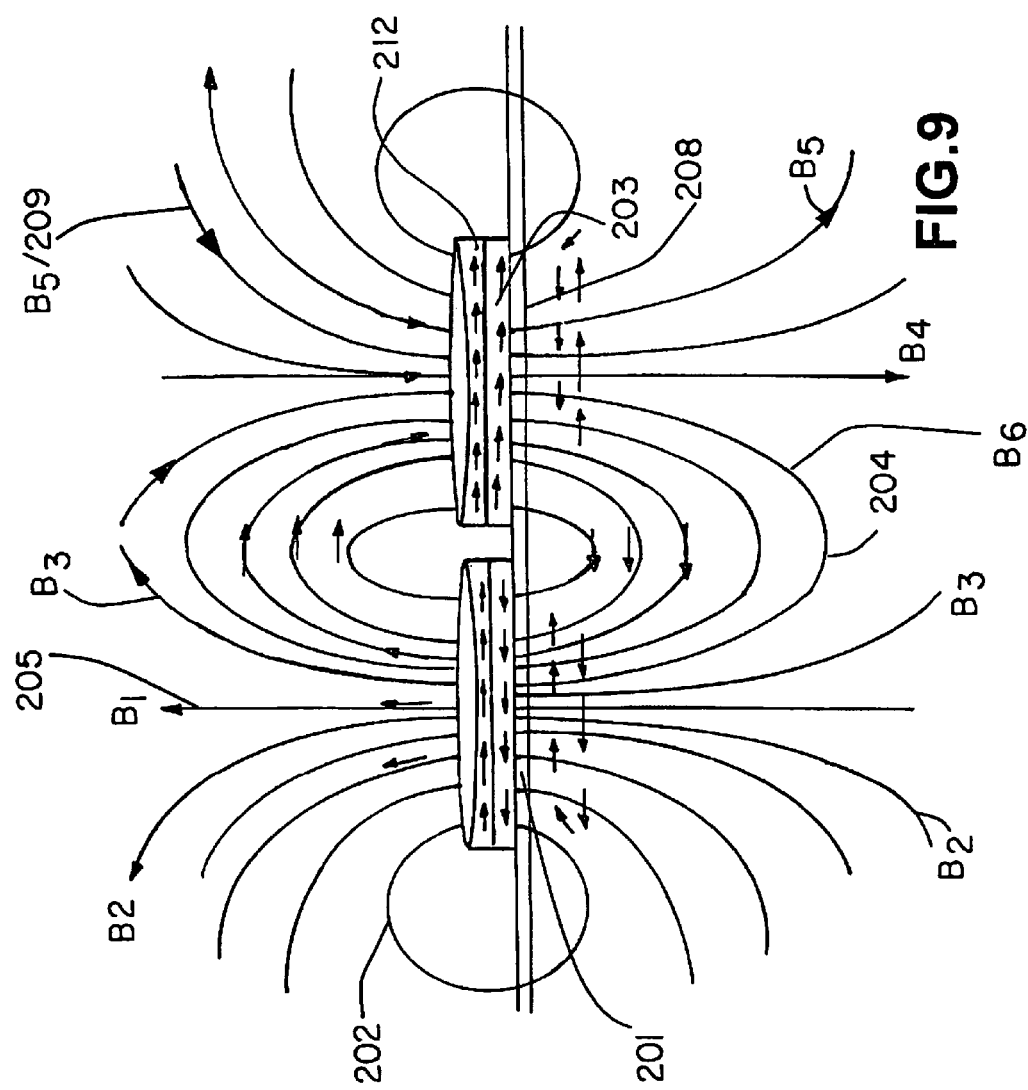
FIG. 9 is a schematic view of an alternative embodiment of the coil position of the assembly.

FIG. 9 illustrates an alternate embodiment 201/212 of the coils and ferrite structure of the embodiments of FIGS. 6-8. This embodiment differs from that of the previous embodiment only in the number of coils in the inductors. Such a change in the number of coil turns will produce differences in the strength and geometry of resultant magnetic fields B1 to B6. FIG. 9 also shows the continuity between field B2 of coil 211 and field B6 of coil 212. Arrows inside the coils show the direction of current flow therein.

Figure 10:
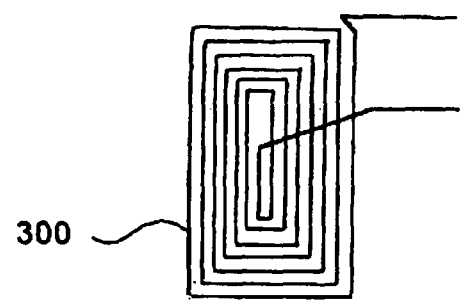
FIG. 10 is a schematic view of another embodiment of the coil portion.

FIG. 10 illustrates a planar coil 300 which may also be used in lieu of coils 102/112 of the embodiment of FIGS. 6-8 or coils 201/202 of the embodiment of FIG. 9. Such planar coils produce transversely directed magnetic fields which are essentially planar as they project outwardly from the plane of coil 300. Such a geometry, while producing weaker magnetic fields, will nonetheless produce fields which are more precisely transverse to the direction of electrical pulses 112 (see FIGS. 6 and 11), thereby enabling the generation of a more precise ExB vector force. Such a provision of precise cross-vector forces may be significant in the treatment of certain conditions.

As to mechanism of operation of pulsed AC field 112 and its induced magnetic field B7 (see FIG. 6), as augmented by the above-described of magnetic fields B2-B6 of the system, it operates to influence the above-described voltage gradient associated with the calcium anions (see FIGS. 1-5) which are the final transmitter of electrical signals of human cells. Studies, as set forth in the Background of the Invention, relate the extent of passage of calcium and other anions through the ionic channels of the cell as it relates to the nerve and metabolic processes that cause many tissue and cell dysfunctions. Therein, many forms of cellular dysfunction have been related to the electrical call to action of cells upon sensing of the voltage gradient, the cell membrane required to open the ionic channels. As such, electrical signals are modulated by the flow of calcium anions from and to the external medium thus affecting intra-cellular storage. Correction of any malfunction in the ability of the cell to provide a proper signal is summarized in FIG. 1 and shown schematically in FIG. 2. The present invention thereby provides necessary currents and voltages, as summarized in FIGS. 3, 4 and 5, necessary to optimize the flow of calcium anions to thereby restore normal function of dysfunctional cells within a given tissue. It is to be appreciated that other anions and their channels, e.g., potassium or sodium channels, may be associated with a given dysfunction.

Figure 11:
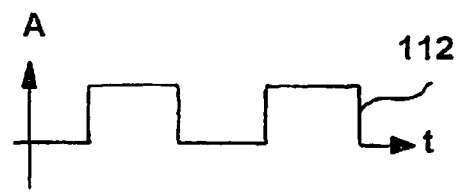
FIG. 11 is a view of AC EMF pulse packets emitted by the spherical probe of the assembly to locate a source of cell dysfunction.
Figure 12:
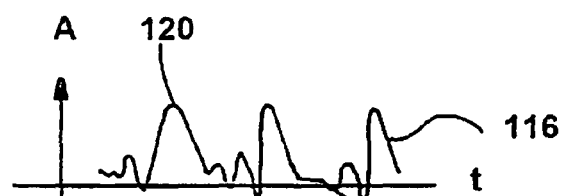
FIG. 12 is a view of pulse packets emitted by damaged tissue at initiation of treatment.

Shown in FIG. 11 is a waveform of a type used during initial probe emission, that is, when searching for a source of dysfunction. FIG. 12 shows a waveform that is received when a source of dysfunction is located. responsive to waveform of an initial probe emission.

Figure 13:
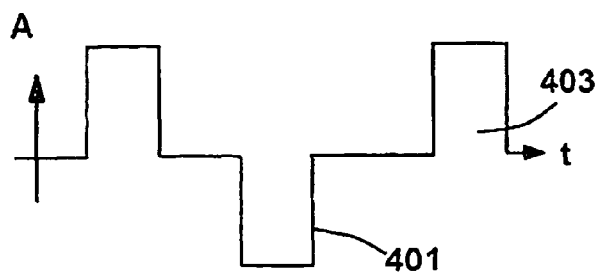
FIG. 13 is a view of representative pulse packets emitted by the spherical probe, used at the initiation of a treatment process.

FIG. 13 is a waveform typical of the type used at the start of treatment using probes of the type shown in FIGS. 6 and 7. This waveform includes a lower portion 401 and upper portion 403 which, it is to be appreciated, may be varied in shape dependent upon the needs of a given condition.

Figure 14:
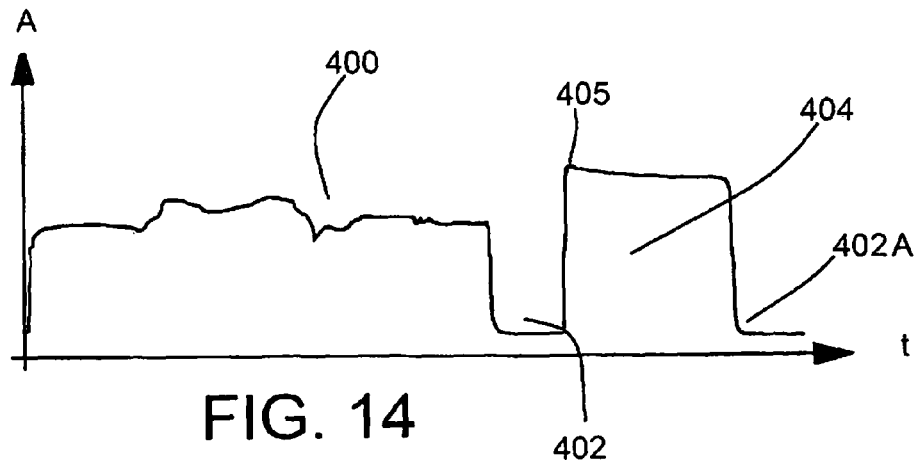
FIG. 14 shows a responsive waveform of a first target tissue locus responsive to the treatment signal of the type of FIG. 13.

FIG. 14 is a waveform of an initial responsive following the beginning of treatment at a target site. Shown is the amplitude of a weaker segment 400 of the responsive wave, followed by transition 402 to a second segment 404 of the responsive waveform, which is stronger or healthier, which is followed by a further transition 402A. Edge 405 of waveform 404 is indicative of a higher capacitance part of the target site.

Figure 14A:
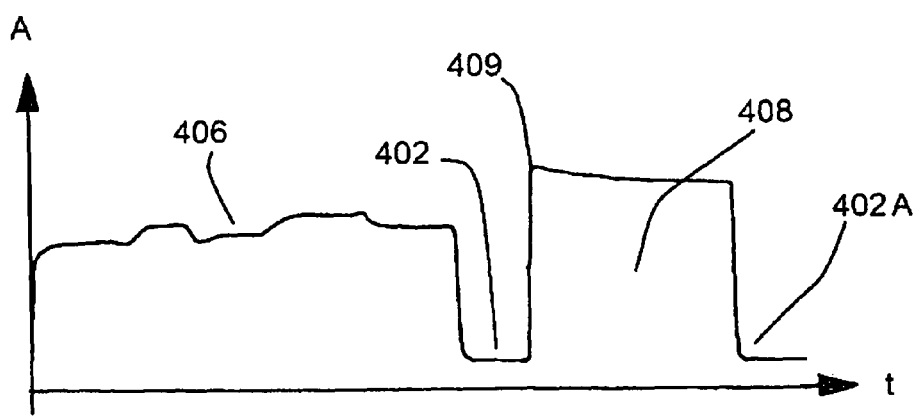
FIG. 14A is the view of a waveform, sequential to that of FIG. 14, however showing changes in the responsive waveform at the first locus of treatment resultant of application of electrical and magnetic fields produced by the probes shown in FIGS. 6, 25 and 26.

FIG. 14A is a view, sequential to that of FIG. 14, showing the result of initial treatment site at a first. Therein is shown that the amplitude of segment 400 of FIG. 14 has now increased to segment 406 of FIG. 14A. This increased height waveform, as well as increased uniformity of the geometry of the waveform is indicative of an induced healing process. Further is an area in which the portion 404 of FIG. 14 has changed to segment 408 shown in FIG. 14A. This is indicative of a greater duration and size which are indicative of healing at the site. Also shown is edge 409. The reduction in sharpness of edge 409 of segment 408 of the waveform indicates healing relative to the edge 405 in segment 404 of the waveform of FIG. 14.

Figure 15:
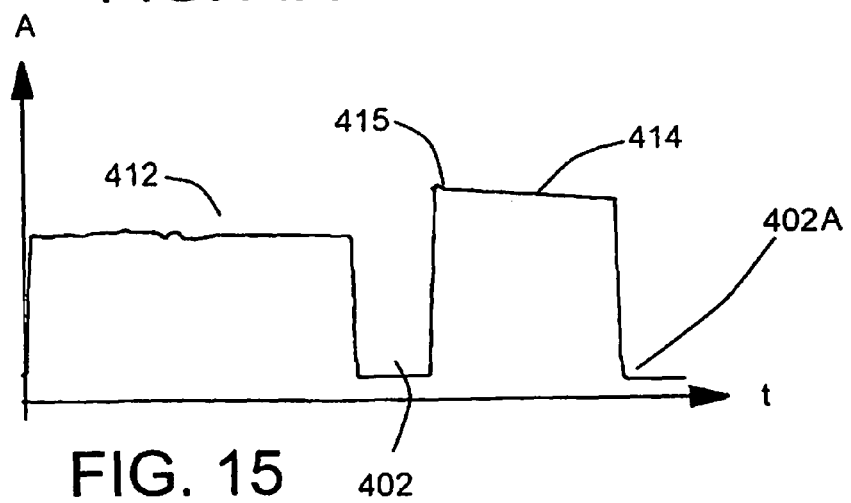
FIG. 15 shows a waveform similar to that of FIGS. 14 and 14A however at a time later in the treatment process.

FIG. 15 is a view further sequential to that of FIG. 14A which shows the manner in which segment 412 of the waveform is now increased substantially in uniformity and strength relative to the initial appearance 400 of the same portion of the responsive waveform. Similarly, waveform 414 has not substantially increased in uniformity relative to corresponding earlier segments 404 and 408. Also, the original edge 405 is flattened as shown at edge 415, this indicative of stability of the capacitance of the treatment site which is desirable for ionic flow stability at afflicted cells.

Figure 16:
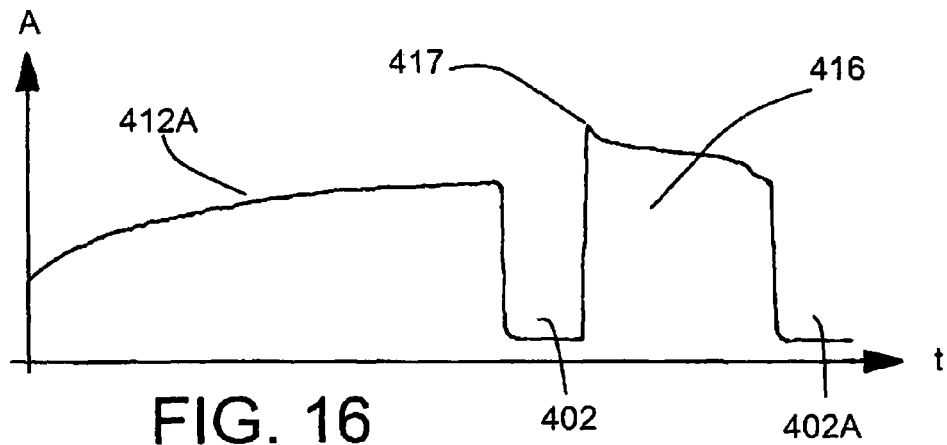
FIG. 16 shows a waveform sequential to that shown in FIG. 15.

FIG. 16 is a view sequential to that of FIG. 15 showing the manner in which waveform 412 has now become more uniform in segment 412A. Segment 416 of FIG. 16 indicates a slight weakening in that responsive area and sharpening of edge 417. This indicates that the treatment is slightly weakening in one area or cell group of the treatment but is retaining its basic positive response to the instant therapy.

Figure 17:
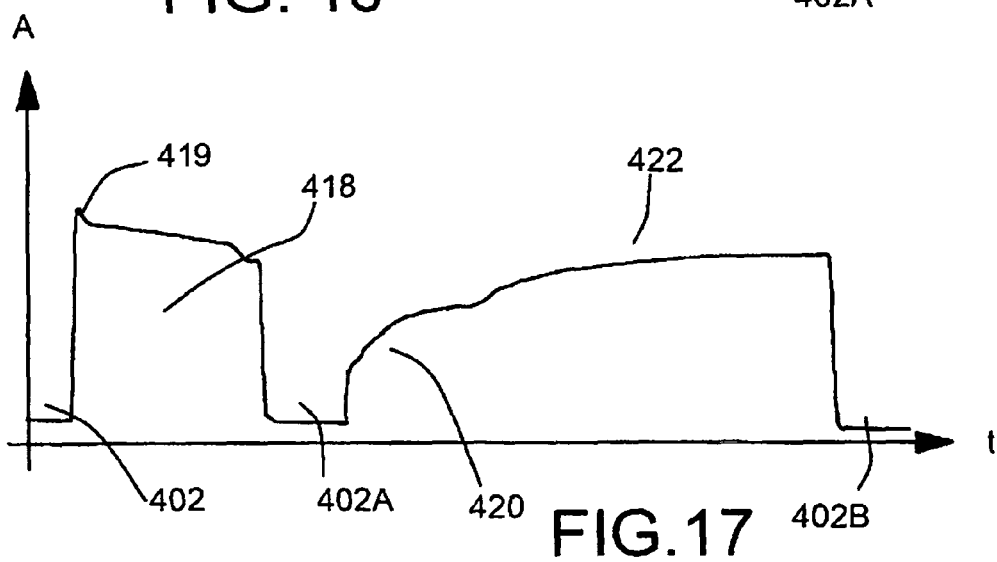
FIG. 17 is a view of a waveform at a second locus of the treatment site.

Shown in FIG. 17 is a waveform sequential to FIG. 16. Segment 422 indicates a strengthening into a healthier pattern by the applicated therapeutic signal and segment 418 indicates a shorter but stronger response.

Figure 18:
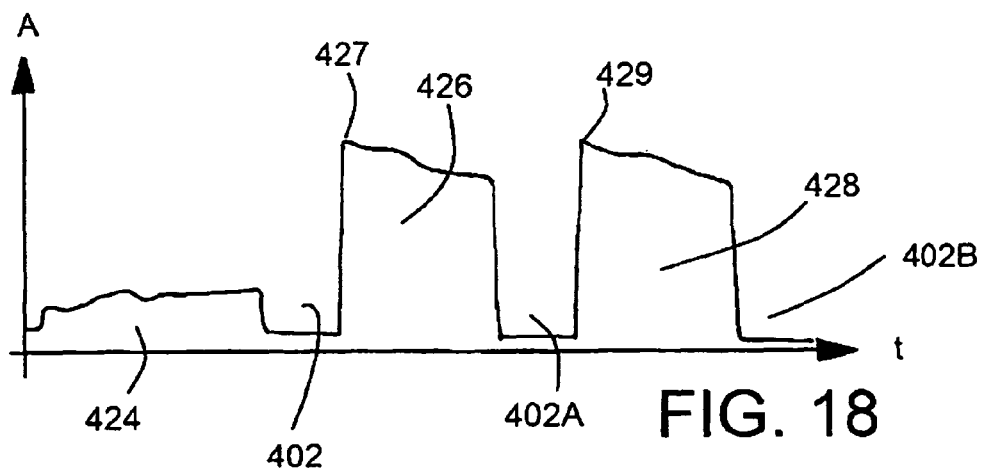
FIG. 18 is a view sequential to that of FIG. 17 showing further changes in the responsive waveform at the second locus of treatment

FIG. 18 is a view at a second locus of treatment showing that the treatment site exhibits an initial weak segment 424 followed by two stronger segments 426 and 428, each of which exhibit high capacitance areas 427 and 429 respectively.

Figure 19:
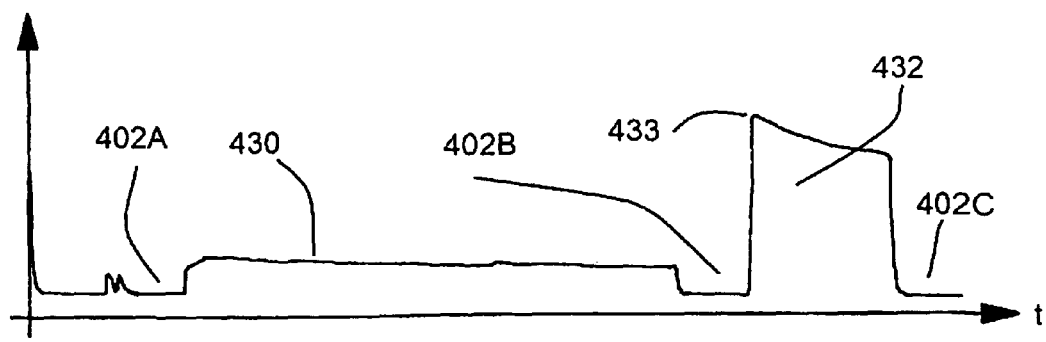
FIG. 19 is a waveform showing an initial response at a third locus of treatment associated with the same pain or tissue dysfunction.

FIG. 19 is a view of a third locus of treatment within the same general therapy area. In other words, once a general healing response is observed both upon the wave form and in audio transform thereof (smooth sound versus static), the treatment probe is moved slightly until another area of malfunction appears visually as a weak signal and in audio as static or screeching sound. Thereafter application of a new complex EM wave and energy pattern of the type shown in FIGS. 6 and 27 is again applied. In FIG. 19 may be seen segment 430 which is indicative of a weak response corresponding to poor ionic flow across afflicted cells. Segment 432 indicates an area of more positive response than that of segment 430.

Figure 20:
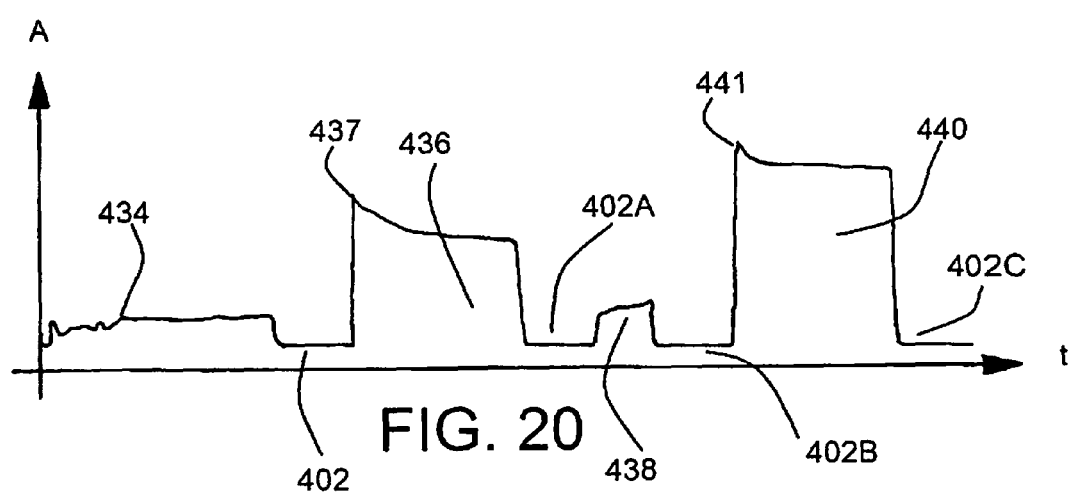
FIG. 20 is a view, sequential to that of FIG. 19 showing changes in tissue in response to the treatment.
Figure 21:
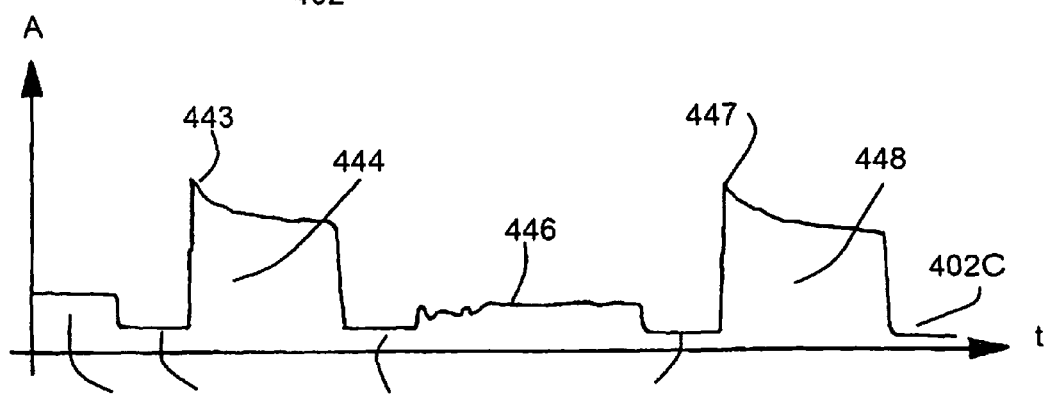
FIG. 21 is a view, sequential to that of FIG. 20 showing further changes at locus three of the treatment site.

FIG. 20 is a waveform sequential to that of FIG. 19 in which segment 430 of FIG. 19 may be seen to have strengthened into waveforms 436 and 438 in which only a particularly weak segment 434 remains of the original long weak portion 430. Further, segment 432 of FIG. 19 has now strengthened into a healthier waveform segment 440 shown in FIG. 20. Pointed edges 437 and 441, shown in FIG. 20, are indicative of rate of change of capacitance at a treatment site, which is not desirable. FIG. 21 is a view, sequential to that of FIG. 20 showing the manner in which responsive waveforms have changed. This waveform shows some weakening of waveform segment 436 into segment 444 shown in FIG. 21 and weakening of segment 440 shown as segment 448 in FIG. 21. Also, the pointed edges of certain waveform segments 444 and 448 have increased, as may be noted by comparing the geometry of waveform segment 437 with that of 443 in FIG. 19. Also, waveform segment 438 of FIG. 20 has changed into segment 446 of FIG. 21. This indicative that a change should be made in the treatment signal as the segment 446 is weakening.

Figure 22:
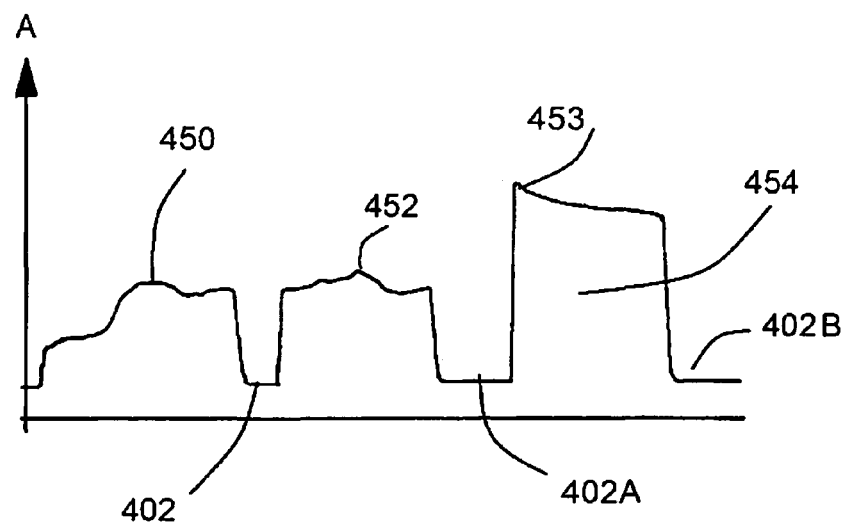
FIG. 22 is a view, sequential to that of FIG. 21 showing yet further changes in the responsive waveform at the third locus of treatment.

FIG. 22 is a view, sequential to that of FIG. 21 showing responsiveness to the treatment signal in the form of increased average amplitude, this indicative of increased ion flow through the channels of cells at the tissue of interest. More particularly, segment 446 of FIG. 21 has strengthened into a healthier response 452 shown in FIG. 22. Segment 448 of FIG. 21 has also strengthened into segment 454 of FIG. 22.

Figure 23:
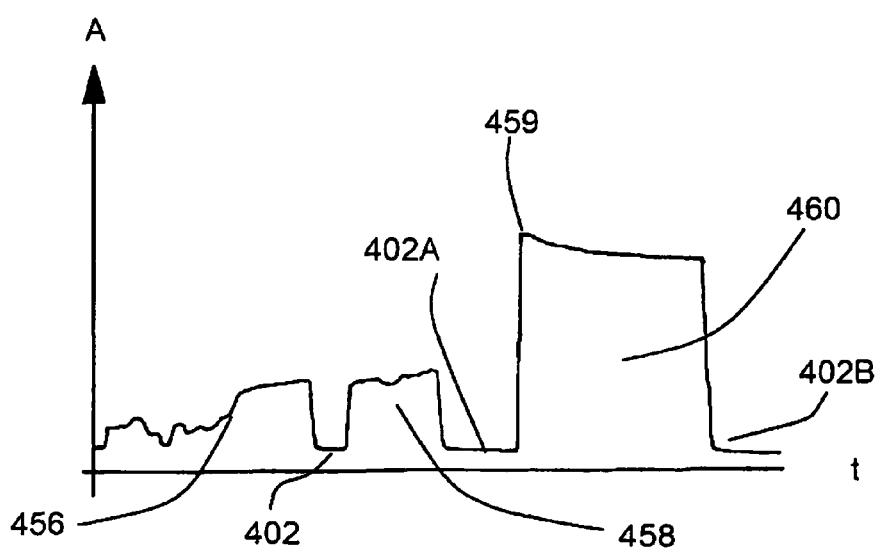
FIG. 23 is a view, sequential to that of FIG. 22 showing the responsive waveform at the third locus of treatment.

FIG. 23 is a view, sequential to that of FIG. 22, showing that the signal segments 450 and 452 of FIG. 22 are unable to hold the healing effect of the applied signal while segment 454 of FIG. 22 is able to do so over a longer period, morphing into segment 460 while the edge 459 thereof is less acute than that of edge 453 of segment 454 of FIG. 22, this indicating that the therapeutic effect of the applied signal is holding at the cell grouping between transitions 402 and 402A in FIGS. 22 and 23 respectively.

Figure 24:
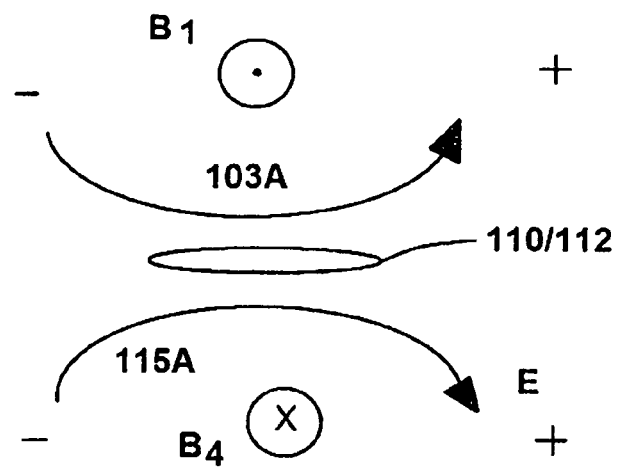
FIG. 24 is a top plan conceptual view taken along Line 24-24 of FIG. 6 showing the manner in which concentric electric fields associated with the B1 and B4 fields of the respective coils 102 and 112 produce electrical re-inforcement effects of E fields induced by the B fields.

FIG. 24 is a top plan conceptual view taken along Line 24-24 of FIG. 6, this showing the manner in which magnetic fields B1 and B4 have a re-inforcing effect of their induced E fields 103A and 115A at outer edges of the magnetic fields B2 and B5, thereby increasing the effect of spherical probe 110, its pulsed electric field 112, and the spherical induced pulsed magnetic field B7 associated therewith (see FIG. 6).

Figure 25:
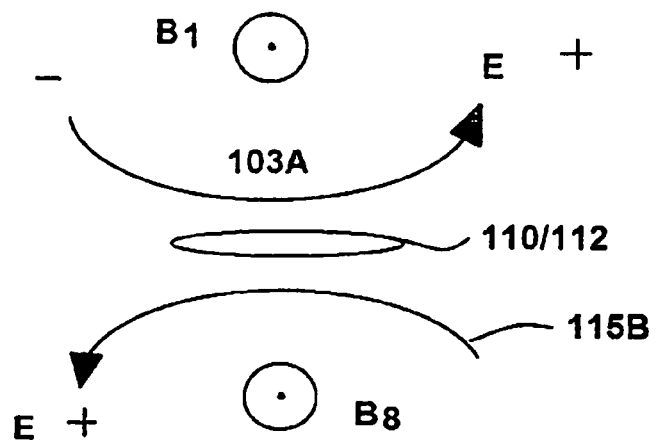
FIG. 25 is a view, similar to that of FIG. 24, however showing the manner in which the induced electric fields E associated with the axial magnetic fields B1 and B8 of the respective coils cancels each other if current is reversed through coil 112, reversing axial magnetic field B4.

Shown in FIG. 25 is a view in which the direction of current flow 103 within windings 112 about ferried core 108 (see FIGS. 6 and 7) has been reversed such that the flow of current therein is in the same direction as that of coil 102 about ferrite core 101 at the left of probe 107 shown in FIGS. 6 and 7. When this is done, FIG. 25 indicates that a cancellation of the electric fields 103A and 115B responsive to magnetic fields B1 and B8. That is, magnetic fields B8 produce a cancelling electrical effect relative to the electrical field of B1. It is therefore, to be appreciated that the electromagnetic properties of treatment waves may be varied as a function of the directionality of current 103/115 which flow through coils 102 and 118 about the ferrite cores 108. See FIGS. 6 and 8. These current flows as to core 108 are shown as 115A in FIGS. 24 and 115B in FIG. 25.

Figure 26:
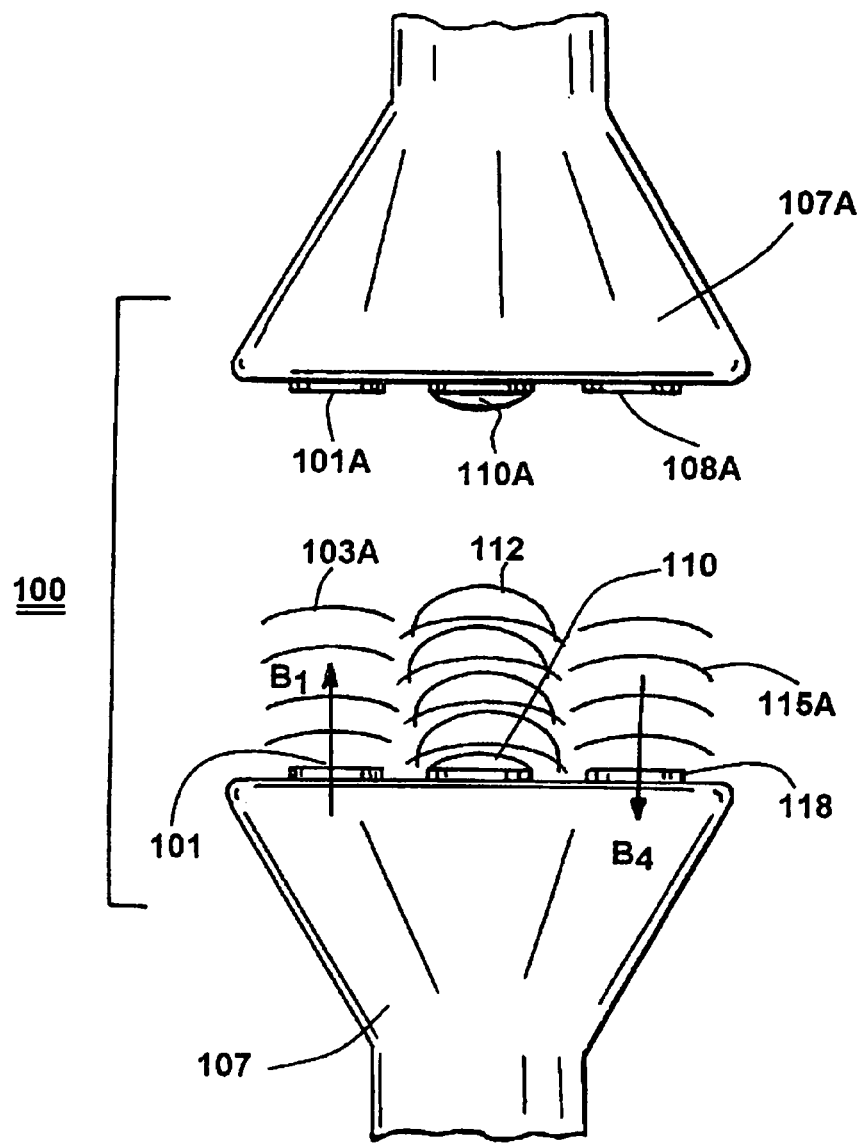
FIG. 26 is a view, similar to FIG. 6, however showing a complete treatment unit consisting of substantially identical upper and lower probes to those described in connection with said FIG. 6.

Shown in FIG. 26 is a view similar to that of FIG. 6, however showing that, in most applications, a second treatment probe 107A will also be used in system 100 which, generally, will be identical to that of lower probe 107. Use of two such probes is often necessary to locate and treat afflicted areas having a particular geometry, size or location.

Figure 27:
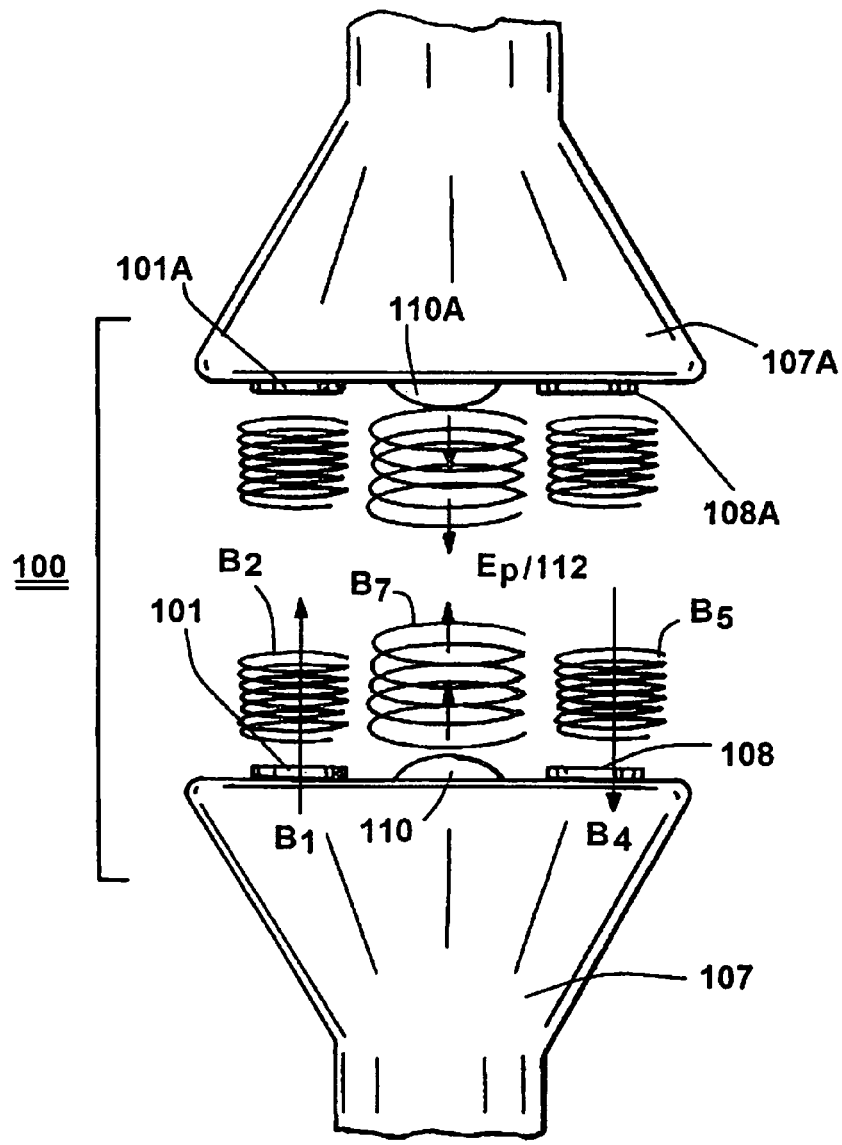
FIG. 27 is a view, similar to FIG. 26, however showing more details of the magnetic and electrical fields associated with the respective probes.

FIG. 27 is a view, similar to that of FIG. 26, however showing in more detail the electrical and magnetic fields associated with the present system.

Figure 28:
FIG. 28 is a flow diagram showing the manner in which the complex energy fields shown in FIGS. 6 and 27 when applied to a target tissue may be used to create three-dimensional images relative to the ionic functions of the treated cells.
Figure 29:
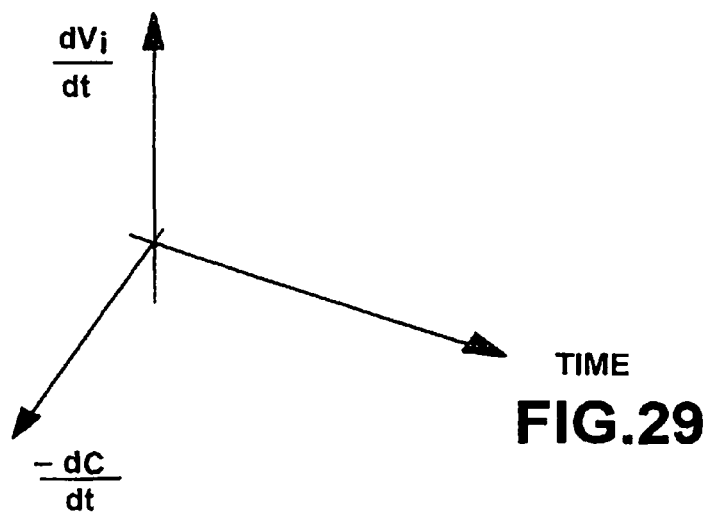
FIG. 29 is a conceptual view of parameters which may be visually displayed to form a three dimensional image which relates to the velocity of anion transport function of cells of the target tissue and rate of capacitative change at the target tissue. One map also map voltage of ion transport at treatment site and signal stability at treatment site in a three-dimensional format relative to the initial responsive signal data over the period of treatment.

FIG. 28 is a block diagrammatic view showing how, by the input of a complex electrical and magnetic signals, shown in FIGS. 6 and 27, to a tissue site of interest, a three-dimensional image based upon a map of any selectable two of the following parameters, against time, may be accomplished, namely, signal stability or rate of change in amplitude of signals as discussed above relative to FIG. 14-23. One may also calculate the first or second derivative of the absolute signal amplitude as a more precise measure of signal stability. Capacitance is a further parameter that may be mapped against time to show how the effects of the treatment signal are retained at the treatment site. The derivative of capacitance may be mapped to show the rate of discharge of capacitance. Also, voltage across the cell membrane at the treatment site may, as in the view of FIG. 5, be used as an important parameter, in combination with others, to produce two or three dimensional imaging of value to the treating technician and physician. The rate of change of voltage across cell membrane is also an important parameter which may be mapped both to provide a more complete picture of a user dysfunction and the result which the present therapy is effecting during treatment and between treatment session. An example of useful parameters which may be mapped in three-dimensions is shown in FIG. 29.

From the above, the instant invention may be practiced through the use of an EMF probe assembly for the treatment and recognition of abnormalities of nerves and other cells and tissues of the human body including membrane flow of ions of cells associated with such conditions. Such an assembly includes a probe; at least a ferromagnetic core positioned within said probe; and at least one induction coil wound about at least one core. An assembly will typically include a plurality of probes and a corresponding plurality of coils thereabout in which at least one of said cores defines a sphere integral to a core at a distal end of its probe. An electrical pulse train is furnished to a proximal end of at least one of said coils wherein a pulsed magnetic wave is thereby provided along an axis of said cores to the distal ends thereof. Such electrical pulse train therefore generates pulsed magnetic fields axial to said cores and extending as magnetic outputs from the distal ends of the probes. More than one, and preferably two probes are used concurrently such that two geometries of pulsed magnetic fields are emitted from the distal ends thereof. Typically one of such probes would be the above-described probe having a spherical end while the other probe would be a non-spherical probe. As may be appreciated, the use of said sphere is useful in generating magnetic field outputs of the probes having a hemispherical geometry.

In accordance with the medical principles of treatment discussed above, the pulsed magnetic field output of the probes is preferably of an opposing electron-magnetic polarity to that generated by abnormal tissue to be treated. Thus provided is a means for generating a pulsed electromagnetic field, at a distal end of the at least one of said probes, having a countervailing electro-magnetic geometry to that generated by an abnormal flow of electrons across said cell membranes of a given tissue. The invention, as above described, also includes an audio transform for expressing electromagnetic changes and responses of abnormal cells and tissues into human audible frequencies. Using such frequencies, one may adjust the magnitude and geometry of the above-described electro-magnetic field outputs of the probes. Audio software recognition, as well as clinical training of technicians, enables one to recognize the meaning of the human audible frequency outputs as correlating to desirable or undesirable voltage gradients across cell membrane of cells of an afflicted tissue. The visual means may, similarly, be provided for the viewing of the reactive parameters of the countervailing electro-magnetic geometric provided in the present therapy and by the afflicted tissue.

Accordingly, while there has been shown and described the preferred embodiment of the invention is to be appreciated that the invention may be embodied otherwise than is herein specifically shown and described and within said embodiment, certain changes may be made in the form and arrangement of the parts without departing from the underlying ideas or principles of this invention.

The invention claimed is:

1. An EMF probe assembly for treatment and recognition of abnormalities of nerve and other cells of the human body including cellular trans-membrane flow of ions associated with such abnormalities, the assembly comprising:
  (a) at least one probe, each including a substantially linear conductive element having an axis and a flow of electrical current therethrough, said current producing a magnetic field about said conductive element, said probe emitting an axially projected electrical field at distal end in the direction of treatment of said at least one probe;
  (b) at a radius from the axis of each probe within said assembly, at least one elongate magnetic core from each probe projecting in the direction of treatment from each probe; and
  (c) an induction coil wound about said at least one core of each probe, and having an electric current passing between proximal and distal ends of said coil, said coil generating a magnetic field between opposite poles of each core, said magnetic field in communication with said axially emitted electrical field at said distal end of said conductive element of said probe to produce a therapeutic ExB vector force between magnetic fields of said core and of said electrical field of said conductive element of the probe that exist substantially at right angles to each other.

2. The assembly as recited in claim 1, said in which at least one core defines at least a partial sphere at a distal end thereof.

3. The assembly as recited in claim 2, comprising:
An electrical pulse train for simultaneously emitting a pulsed magnetic field from said spherical end of one probe and from at least one non-spherical distal end of another probe.

4. The assembly as recited in claim 3 in which said induction coils comprise:
means for generating axial magnetic fields and, in combination with said at least one spherical end of one probe, for also generating hemispherical fields.

5. The assembly as recited in claim 1 in which at least one of said cores includes a pivot point within an axis thereof by which an axis of said magnetic field thereof may be tilted relative to said pivot point.

6. The assembly as recited in claim 1, in which said electrical current within said coil of said at least one core comprises:
an electrical pulse train furnished to a proximal end of at least one of said coils, wherein a pulsed magnetic wave is thereby provided along an axis of said cores and distal ends thereof.

7. The assembly as recited in claim 6, in which said electrical pulse train generates pulsed magnetic fields at distal ends of said at least one of said cores.

8. The assembly as recited in claim 7, comprising:
means for simultaneously emitting pulsed magnetic fields from said distal end of at least two probes.

9. The assembly as recited in claim 7, comprising:
means for generating a pulsed magnetic field of opposing magnetic polarity to that generated by abnormal tissue to be treated.

10. The assembly as recited in claim 6, further comprising:
an audio transform for expressing electro-magnetic changes and responses of abnormal cells and tissues into human audible frequencies.

11. The assembly as recited in claim 10, further comprising:
means for adjusting the amplitude of said pulsed electro-magnetic fields in response to said audible frequencies.

12. The assembly as recited in claim 11, in which said audio transform comprises:
means for recognition of said responses of abnormal cells as a function of undesirable voltage gradients across cell membranes of an abnormal tissue.

13. The assembly as recited in claim 10, in which said audio transform comprises:
means for recognizing cell disorders as a function of particular voltage gradients across membranes of cells of abnormal tissue.

14. The assembly as recited in claim 6, further comprising:
means for adjusting said electro-magnetic fields in response to an EM field spectrograph of a tissue abnormality.

15. The assembly as recited in claim 6, comprising:
means for viewing reactive parameters of said countervailing electromagnetic geometry.

16. The assembly as recited in claim 7, comprising:
(a) a magnetometer for monitoring magnetic fields associated with an abnormal flow of ions across cell membranes of a tissue to be treated,
(b) an electrical field meter for monitoring electrical fields associated with said abnormal flow of ions across said cell membranes or tissue to be treated; and
(c) a pulsed electro-magnetic field at an end of said distal end of at least one of said probes, having countervailing electro-magnetic values to those measured by said magnetometer and electrical field meter as generated by said abnormal flow of ions across said cell membranes of the tissue to be treated.

* * * * *